(12) United States Patent
Murakami (10) Patent No.: US 7,044,943 B2
(45) Date of Patent: May 16, 2006

(54) LASER TREATMENT APPARATUS

(75) Inventor: Naho Murakami, Hoi-gun (JP)

(73) Assignee: Nidek Co., Ltd., Gamagori (JP)

(*) Notice: Subject to any disclaimer, the term of this patent is extended or adjusted under 35 U.S.C. 154(b) by 154 days.

(21) Appl. No.: 10/765,971

(22) Filed: Jan. 29, 2004

(65) Prior Publication Data

US 2004/0186462 A1  Sep. 23, 2004

(30) Foreign Application Priority Data

Jan. 31, 2003  (JP) .............................. 2003-023315

(51) Int. Cl.
*A61F 9/08* (2006.01)
*G02B 26/02* (2006.01)

(52) U.S. Cl. ............................................. 606/4; 606/6
(58) Field of Classification Search .................. 605/5; 362/552
See application file for complete search history.

(56) References Cited

U.S. PATENT DOCUMENTS

| | | | | |
|---|---|---|---|---|
| 4,729,372 A | * | 3/1988 | L'Esperance, Jr. ............. | 606/5 |
| 4,732,148 A | * | 3/1988 | L'Esperance, Jr. ............. | 606/5 |
| 4,838,266 A | | 6/1989 | Koziol et al. | |
| 4,911,711 A | * | 3/1990 | Telfair et al. ................... | 606/5 |
| 5,171,242 A | | 12/1992 | Dewey et al. | |
| 5,651,784 A | * | 7/1997 | Klopotek ......................... | 606/5 |
| 6,142,988 A | * | 11/2000 | Strahle et al. .................. | 606/4 |
| 6,238,385 B1 | * | 5/2001 | Harino et al. ................... | 606/4 |
| 6,436,093 B1 | * | 8/2002 | Ruiz et al. ....................... | 606/5 |
| 6,530,918 B1 | * | 3/2003 | Ueno et al. ..................... | 606/10 |
| 6,648,876 B1 | * | 11/2003 | Murakami ....................... | 606/4 |
| 6,679,876 B1 | * | 1/2004 | Kondo et al. ................... | 606/5 |
| 2002/0068925 A1 | | 6/2002 | Murakami | |

FOREIGN PATENT DOCUMENTS

JP  A 2001-8945  1/2001
JP  A 2002-165824  6/2002

\* cited by examiner

*Primary Examiner*—Michael Peffley
*Assistant Examiner*—Henry M Johnson, III
(74) *Attorney, Agent, or Firm*—Oliff & Berridge, PLC (57) ABSTRACT

A laser treatment apparatus includes a laser light source and a light guiding optical system, having an optical axis, for guiding a treatment laser beam emitted from the laser light source to a treatment part. The light guiding optical system includes: an optical fiber through which the treatment beam emitted from the laser light source is guided; a variable magnification optical system which changes a magnification of an image of an exit end face of the optical fiber to be formed on the treatment part in order to change a size of an irradiation spot of the treatment beam on the treatment part; and a beam-attenuating member having a transmittance property that a transmittance is lower in a center portion than in a peripheral portion, the beam-attenuating member being placed in a position on the optical axis where an on-axis luminous flux and an off-axis luminous flux of the treatment beam emerging from the exit end face of the optical fiber pass through the beam-attenuating member at different ratios.

10 Claims, 7 Drawing Sheets

LASER TREATMENT APPARATUS

BACKGROUND OF THE INVENTION

1. Field of the Invention

The present invention relates to a laser treatment apparatus for performing treatment by irradiating a part to be treated (an affected part) with a treatment laser beam.

2. Description of Related Art

Laser treatment apparatuses for a photocoagulation treatment include an apparatus of a parfocal type constructed to form an image of an exit end face of an optical fiber which guides a treatment laser beam (hereinafter, a treatment beam) emitted from a laser light source on a part to be treated (hereinafter, a treatment part), thereby irradiating the treatment part with the treatment beam. When an intensity distribution (i.e., an energy distribution) of the treatment beam at the exit end face of the optical fiber is uniform, this parfocal type apparatus provides a uniform intensity distribution of the treatment beam on an irradiation plane of the treatment part. However, in a retinal photocoagulation treatment, a tissue irradiated does not evenly react even where the intensity distribution at the irradiation plane is uniform, so that a center portion of an irradiation spot tends to first begin to burn (coagulate). In particular, when the size of the irradiation spot of the treatment beam is set at, for example, as large as 500 μm in diameter, the intensity distribution in the irradiation spot has an influence on a coagulation effect. Accordingly, an ideal intensity distribution in a large-sized irradiation spot of the treatment beam has been considered to be high (strong) in a peripheral portion and low (weak) in a center portion. On the other hand, in an iris incision treatment (iridotomy), it is an ideal to set the size of the irradiation spot of the treatment beam at, for example, as small as 50 μm in diameter, thereby increasing an energy density in the irradiation spot.

For example, Japanese patent unexamined publication No. 2001-8945 discloses such apparatus structured to increase or decrease the intensity distribution in the center portion of the irradiation spot as compared with that in the peripheral portion. This apparatus is provided with a filter capable of changing a beam intensity distribution. To change the intensity distribution in the irradiation spot, this filter is attached to a rotatable support board and placed adjacent to the exit end face of the optical fiber. Alternatively, the filter is placed in a position unconjugated with the irradiation plane and moved in an optical axis direction.

In the above conventional apparatus, however, the support board of the beam intensity distribution changing filter placed adjacent to the exit end face of the optical fiber has to be rotated in order to produce different intensity distributions according to spot sizes, large and small. This would lead to a complicated structure, which needs a complex operational control. In this structure, it is uneasy to align the center of the filer with the optical axis during adjustment in each case. The exit end face of the optical fiber and the irradiation plane are positioned to be conjugated with each other, so that slight misalignment of the optical axis would affect the intensity distribution on the irradiation plane. Since the exit end face of the optical fiber is several tens μm in diameter, a light-shielding part of the filter needs to be made very small and therefore it is hard to manufacture.

In the case where the beam intensity distribution changing filter is inserted in a position unconjugated with the irradiation plane, a structure of some kind must be provided to move the filter in the optical axis direction in order to change the intensity distribution. The apparatus structure would further become complicated.

SUMMARY OF THE INVENTION

The present invention has been made in view of the above circumstances and has an object to overcome the above problems and to provide a laser treatment apparatus with a simple structure, capable of irradiating a treatment laser beam at an irradiation intensity distribution appropriate for treatment purposes.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a laser treatment apparatus including: a laser light source, and a light guiding optical system, having an optical axis, for guiding a treatment laser beam emitted from the laser light source to a treatment part, wherein the light guiding optical system includes: an optical fiber through which the treatment beam emitted from the laser light source is guided; a variable magnification optical system which changes a magnification of an image of an exit end face of the optical fiber to be formed on the treatment part in order to change a size of an irradiation spot of the treatment beam on the treatment part; and a beam-attenuating member having a transmittance property that a transmittance is lower in a center portion than in a peripheral portion, the beam-attenuating member being placed in a position on the optical axis where an on-axis luminous flux and an off-axis luminous flux of the treatment beam emerging from the exit end face of the optical fiber pass through the beam-attenuating member at different ratios.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
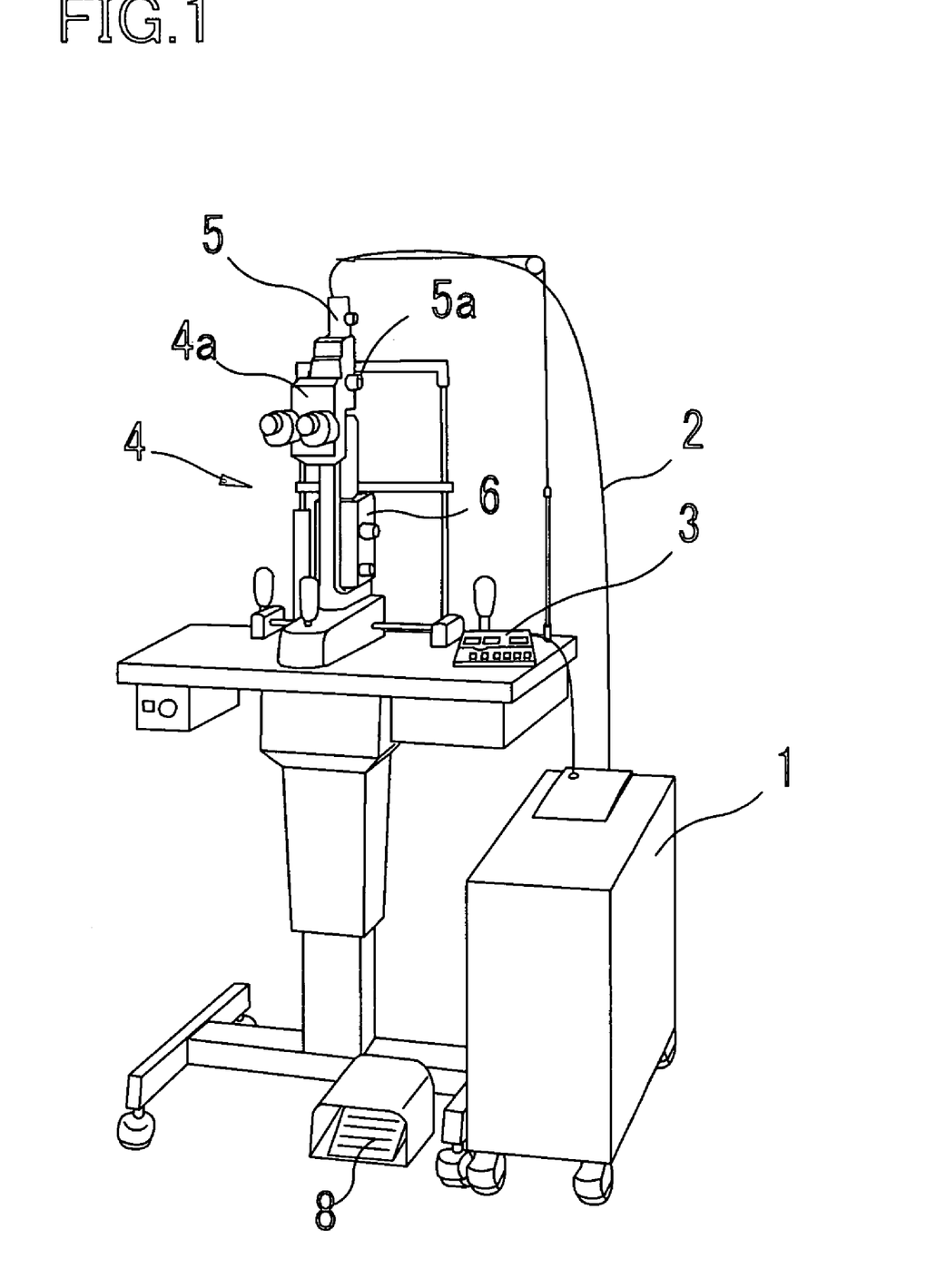
FIG. 1 is a schematic external view of a laser treatment apparatus in a preferred embodiment.
Figure 2:
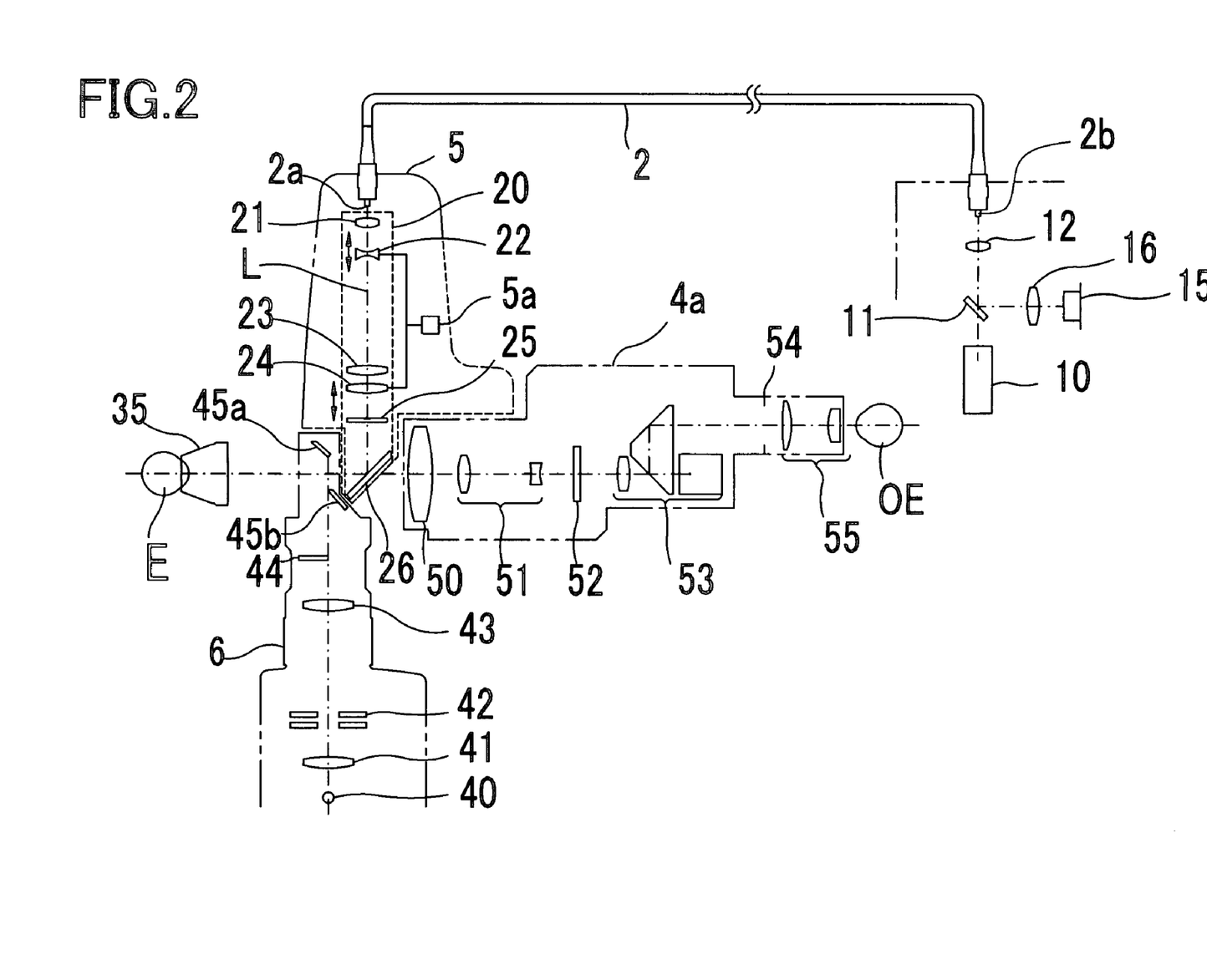
FIG. 2 is a schematic structural view of an optical system of the present apparatus.

A detailed description of a preferred embodiment of a laser treatment apparatus embodying the present invention will now be given referring to the accompanying drawings. FIG. 1 is a schematic external view of the laser treatment apparatus for performing treatment on a patient's eye. FIG. 2 is a schematic structural view of an optical system of the apparatus.

A main unit 1 of the apparatus is internally provided with a laser light source 10 for treatment, a laser light source 15 for aiming, and an optical system for introducing a treatment laser beam and an aiming laser beam into an optical fiber 2.

A controller 3 is used to set laser irradiation conditions such as laser power, laser irradiation time (duration), etc. A slit lamp delivery 4 is constructed for performing irradiation of the treatment beam and the aiming beam to a part to be treated (an affected part) of a patient's eye E while allowing an operator to observe the eye E. The slit lamp delivery 4 is provided with an irradiation part 5 for irradiating each laser beam delivered therein through the fiber 2 to the eye E, an illumination part 6 for slit-illuminating the eye E, and a binocular microscope part 4a. A footswitch 8 is used to transmit a trigger signal to perform irradiation of the treatment beam.

In the irradiation part 5 there is provided a spot size adjustment knob 5a to change the size (the diameter) of an irradiation spot of each beam (an image of an exit end face 2a of the fiber 2) to be irradiated to (formed on) the treatment part of the eye E. By operation of the adjustment knob 5a, the spot size of each beam can be changed in a range of 50 µm to 500 µm in diameter.

The treatment beam emitted from the light source 10 is condensed on an inlet end face 2b of the fiber 2 by a condensing lens 12 and therefrom enters the fiber 2. A dichroic mirror 11 is placed between the light source 10 and the condensing lens 12. The aiming beam emitted from the light source 15 passes through a collimator lens 16 and then is made coaxial with the treatment beam by the dichroic mirror 11. It is to be noted that, as the light source 10 used in the present embodiment, an Nd:YAG laser capable of oscillating a fundamental wave of 1064 nm is used to generate a green light of 532 nm, which is double the fundamental wave. As the light source 15, a laser diode which emits a red light of 630 nm is used.

The treatment beam and the aiming beam are guided through the fiber 2 to the irradiation part 5. An intensity distribution of the treatment beam emerging from the exit end face 2a of the fiber 2 is substantially uniformized through the fiber 2. The irradiation part 5 internally holds an irradiation optical system 20 for guiding each beam emerging from the exit end face 2a to a target (a fundus, an iris, and others, of the eye E). The irradiation optical system 20 is provided with a condensing lens 21, a lens 23, zoom lenses 22 and 24, a beam-attenuating plate 25, and a movable mirror 26 for changing an irradiation direction of each beam. The zoom lenses 22 and 24 are allowed to move in an optical axis L of the optical system 20 by operation of the adjustment knob 5a, thereby changing a magnification of an image to be formed. Each beam is irradiated to the fundus of the eye E through a contact lens 35.

Figure 3:
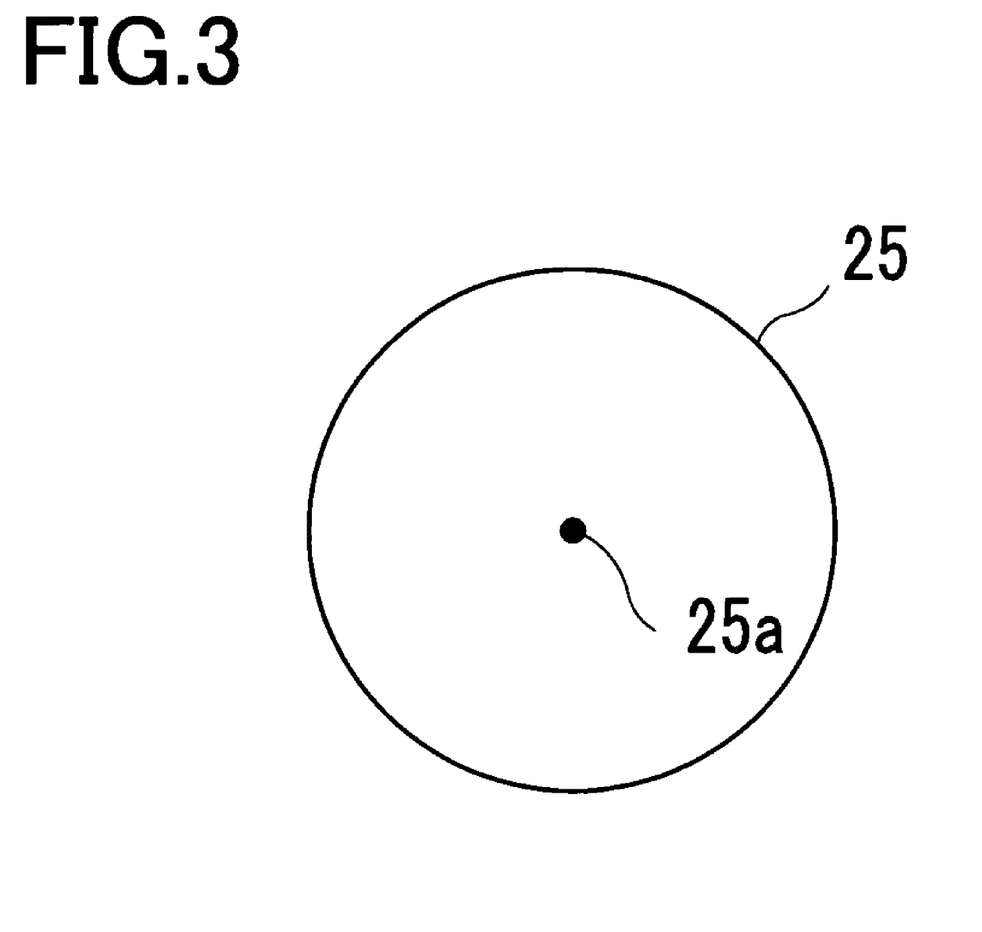
FIG. 3 is a structural view of a beam-attenuating plate.

The beam-attenuating plate 25 is a beam-attenuating member having a transmittance property that a center portion is lower in transmittance than a peripheral portion. In the present embodiment, as shown in FIG. 3, the attenuating plate 25 is a transparent glass plate provided centrally with a shielding part 25a which attenuates 100% of the treatment beam. The shielding part 25a is provided on the optical axis L. The attenuating plate 25 is placed in a position on the optical axis L, other than the vicinity of the exit end face 2a of the fiber 2 and its conjugated position, so that the on-axis luminous flux and the off-axis luminous flux of the treatment beam emerging from the exit end face 2a pass through the attenuating plate 25 at different ratios. This shielding part 25a is a black point of 1.5 mm in diameter, coated on the attenuating plate 25. The size of the shielding part 25a is determined enough to block a part of the on-axis luminous flux (see FIGS. 4A and 5A).

In the illumination part 6, an illumination light source 40 is placed. Illumination light from the illumination light source 40 passes through a condensing lens 41, a slit plate 42, and a projection lens 43, and is reflected by a splitting mirrors 45a and 45b to illuminate the eye E. A correcting lens 44 is used to correct the length of an optical path of the illumination light reflected by the splitting mirrors 45a and 45b. In addition, the binocular microscope part 4a is provided with an objective lens 50, a variable magnification optical system 51, a protective filter 52, erect prisms 53, a field diaphragm 54, and an eyepiece 55. "OE" denotes an operator's eye.

The operation of the above structured apparatus is explained below.

The operator observes, through the microscope part 4a, the fundus of the eye E illuminated by the illumination light from the illumination part 6. While observing the aiming beam irradiated to the fundus, the operator manipulates the adjustment knob 5a to set a desired spot size.

Figure 4A:
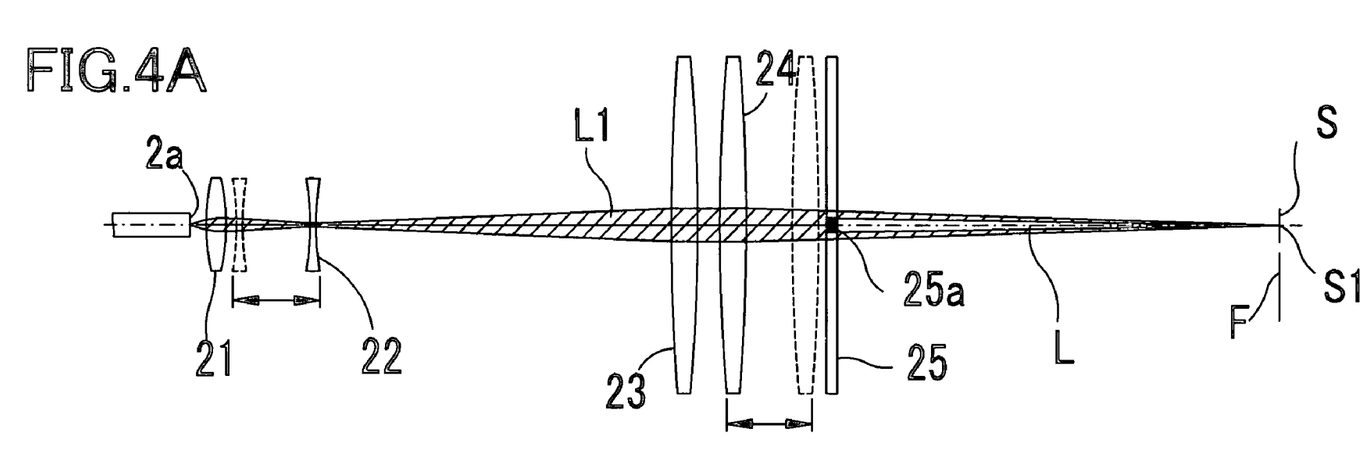
FIGS. 4A and 4B are views showing an irradiation optical system and an on-axis luminous flux and an outermost off-axis luminous flux respectively.
Figure 4B:
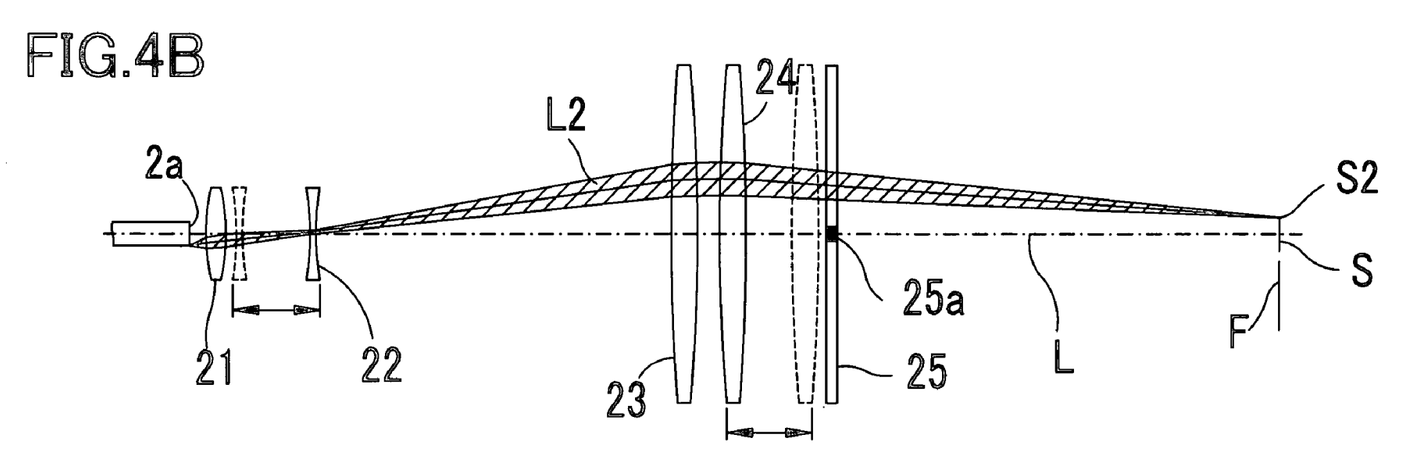

At first, explanation is made on the case where the above apparatus is used for the retinal photocoagulation treatment, in which the spot size is set at as relatively large as 500 µm in diameter. When the spot size is set at 500 µm with the knob 5a, the zoom lenses 22 and 24 are moved to respective predetermined positions (from dotted lines to solid lines) shown in FIGS. 4A and 4B. FIG. 4A shows the on-axis luminous flux L1 of the treatment beam emerging from a center portion of the exit end face 2a of the fiber 2. FIG. 4B shows the outermost off-axis luminous flux L2 of the treatment beam emerging from an end (edge) portion (a lower end (edge) portion in the figure) of the exit end face 2a. In the case of the large spot size, as shown in FIGS. 4A and 4B, in the vicinity of the zoom lens 24, the on-axis luminous flux L1 travels along (on) the optical axis L in a vertical plane to the optical axis L and the outermost off-axis luminous flux L2 travels through off the optical axis L in the vertical plane. The shielding part 25a of the beam-attenuating plate 25 is provided in a position on the optical axis L where the on-axis luminous flux L1 and the off-axis luminous flux including the outermost off-axis luminous flux L2 do not coincide (converge) in the vertical plane. In the optical arrangement in the present embodiment, the position on the optical axis L where the on-axis luminous flux L1 and the off-axis luminous flux coincide (converge) exists near a condensing position of the condensing lens 21 (that is, near the lens 22). The size of the shielding part 25a is determined so that a beam-attenuation ratio at which the shielding part 25a attenuates the on-axis luminous flux L1 corresponds to an intensity ratio between the center portion and the peripheral portion of a desired irradiation spot. For example, if the intended ratio is 1 to 2 between the center portion and the peripheral portion of the irradiation spot of which the spot size is 500 µm in diameter as in the present embodiment, the size of the shielding part 25a is determined so as to offer a 1-to-2 area ratio between the area of the shielding part 25a and the sectional area of the on-axis luminous flux L1 at the position of the shielding part 25a.

Figure 6A:
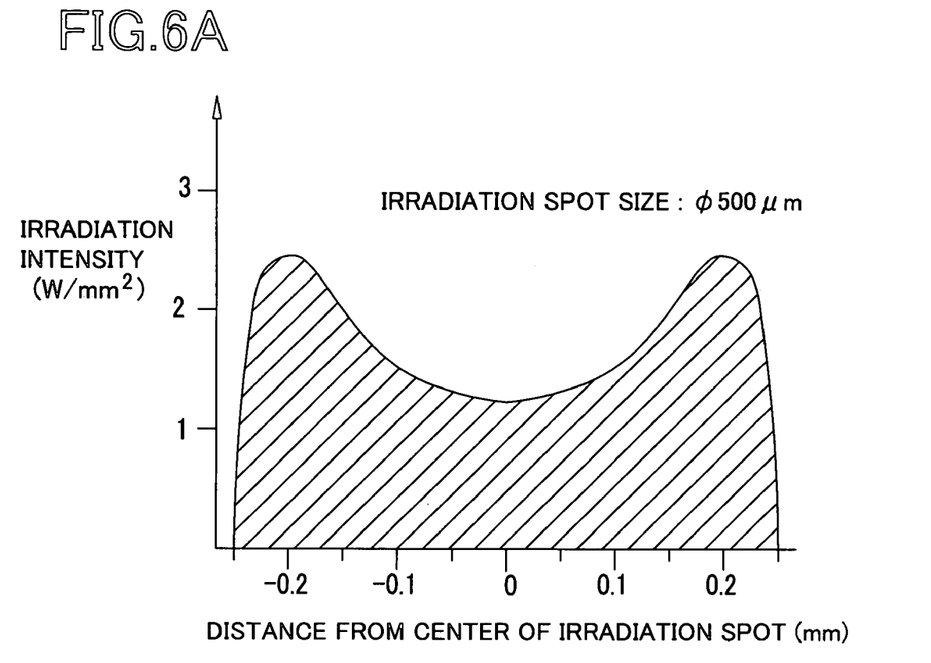
FIGS. 6A and 6B are graphs each showing an irradiation intensity distribution of a treatment laser beam.

Half of the on-axis luminous flux L1 is blocked by the shielding part 25a, while the outermost off-axis luminous flux L2 is fully allowed to travel to an irradiation plane F such as the fundus or the like without being blocked by the shielding part 25a. As shown in FIG. 4A, the on-axis luminous flux L1 that has been allowed to pass through the beam-attenuating plate 25 without being blocked by the shielding part 25a is condensed on a center portion S1 of an irradiation spot S on the irradiation plane F. As shown in FIG. 4B, on the other hand, the outermost off-axis luminous flux L2 is condensed on a peripheral portion S2 of the irradiation spot S. In the beam irradiation intensity distribution in the case of the spot size of 500 μm in diameter, as seen in FIG. 6A, the intensity in the center portion of the irradiation spot S is half the intensity in the peripheral portion. In the photocoagulation by irradiation of the treatment beam to the fundus, consequently, heat is hard to concentrate in the center portion, which makes it possible to prevent the center portion from first beginning to burn. Thus, an evenly burnt photocoagulation plane can easily be formed.

The shielding part 25a is of a size not to block the outermost off-axis luminous flux L2 when the spot size is 500 μm in diameter. Accordingly, the efficient irradiation intensity distribution can be provided without decreasing the intensity in the peripheral portion of the irradiation spot S.

Figure 5A:
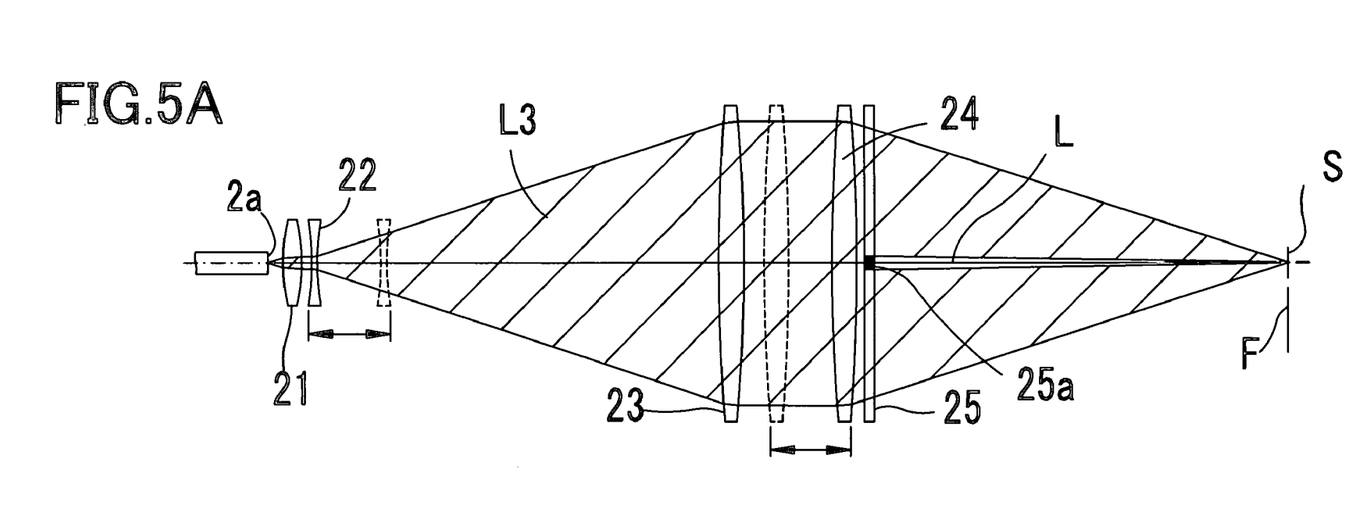
FIGS. 5A and 5B are views showing the irradiation optical system and an on-axis luminous flux and an outermost off-axis luminous flux respectively.
Figure 5B:
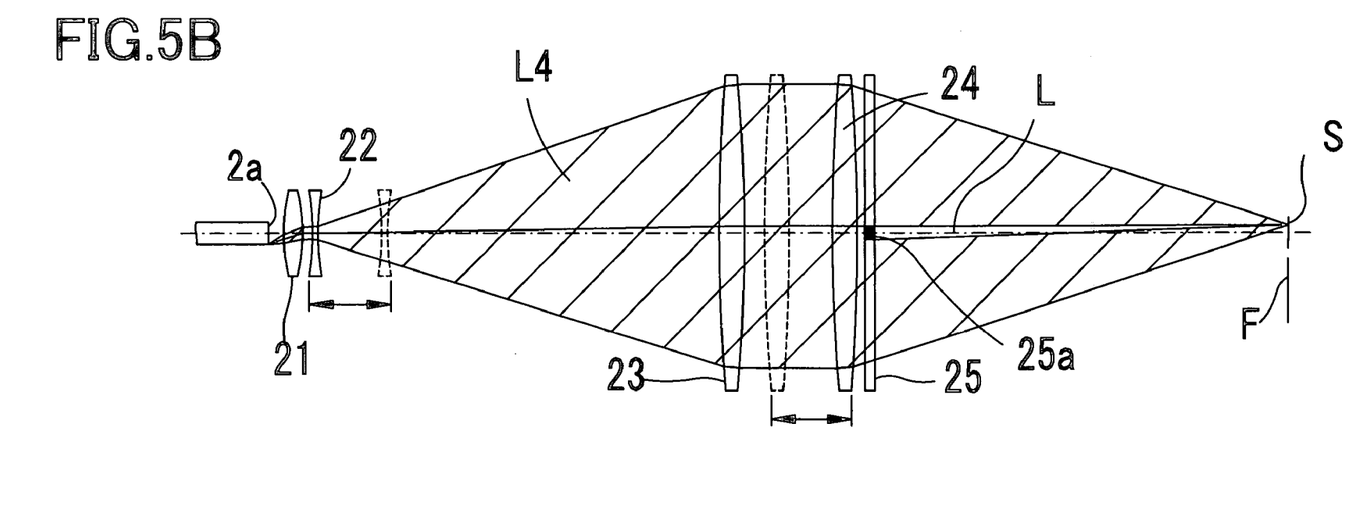

Next, explanation is made on the case where the above apparatus is used for the iris incision treatment (iridotomy), in which the spot size is set at as relatively small as 50 μm in diameter. When the spot size is set at 50 μm in diameter with the knob 5a, the zoom lenses 22 and 24 are moved to respective predetermined positions (from dotted lines to solid lines) shown in FIGS. 5A and 5B. FIG. 5A shows the on-axis luminous flux L3 of the treatment beam emerging from the center portion of the exit end face 2a of the fiber 2. FIG. 5B shows the outermost off-axis luminous flux L4 of the treatment beam emerging from the end (edge) portion (the lower end (edge) portion in the figure) of the exit end face 2a.

As shown in FIGS. 5A and 5B, in the case of the small spot size, the on-axis luminous flux L3 and the outermost off-axis luminous flux L4 are both partially blocked at substantially the same ratio by the shielding part 25a of the beam-attenuating plate 25 placed on the optical axis L. At this time, the shielding part 25a merely blocks the luminous fluxes L3 and L4 at a small quantity of light. The ratio of the blocked light quantity is 1% or less of a total quantity of the luminous fluxes L3 and L4.

Figure 6B:
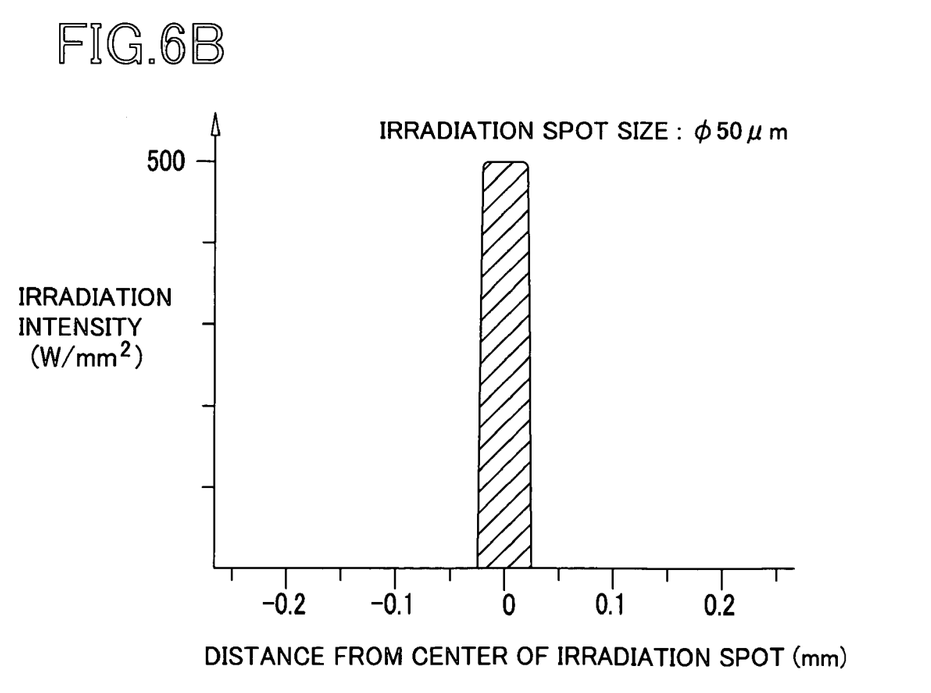

In the case of the spot size of 50 μm, the irradiation intensity distribution of the treatment beam is entirely even as shown in FIG. 6B. In the iris incision, higher laser power is needed as compared with in the retinal photocoagulation, so that it is extremely advantageous that a laser energy loss by the shielding part 25a is 1% or less.

As explained above, when the photocoagulation is conducted with the spot size set to be relatively large, the intensity in the center portion of the irradiation spot is low, which forms an evenly burnt coagulation plane. When the iris incision is performed with the spot size set to be relatively small, the treatment beam can be condensed evenly and thus a hole can efficiently be made in the iris. In this way, the optical system is constructed such that simply changing of the spot size allows changes of the irradiation intensity distribution in the irradiation spot with an appropriate size for treatment purposes. Thus, it is unnecessary to set or adjust each time the optical systems associated with the spot size and the irradiation intensity distribution. The treatments can therefore be performed smoothly.

It is to be noted that, instead of using the beam-attenuating plate 25, the zoom lens 24 may be used for the beam-attenuating member. In this case, the zoom lens 24 is provided, at its optical center, with a shielding part like the shielding part 25a. Moving this zoom lens 24 can produce the same effect as above. Furthermore, when the beam-attenuating member is placed in a position where the on-axis luminous flux and the off-axis luminous flux of the treatment beam pass through at different ratios, the same effect can be brought about.

Figure 7:
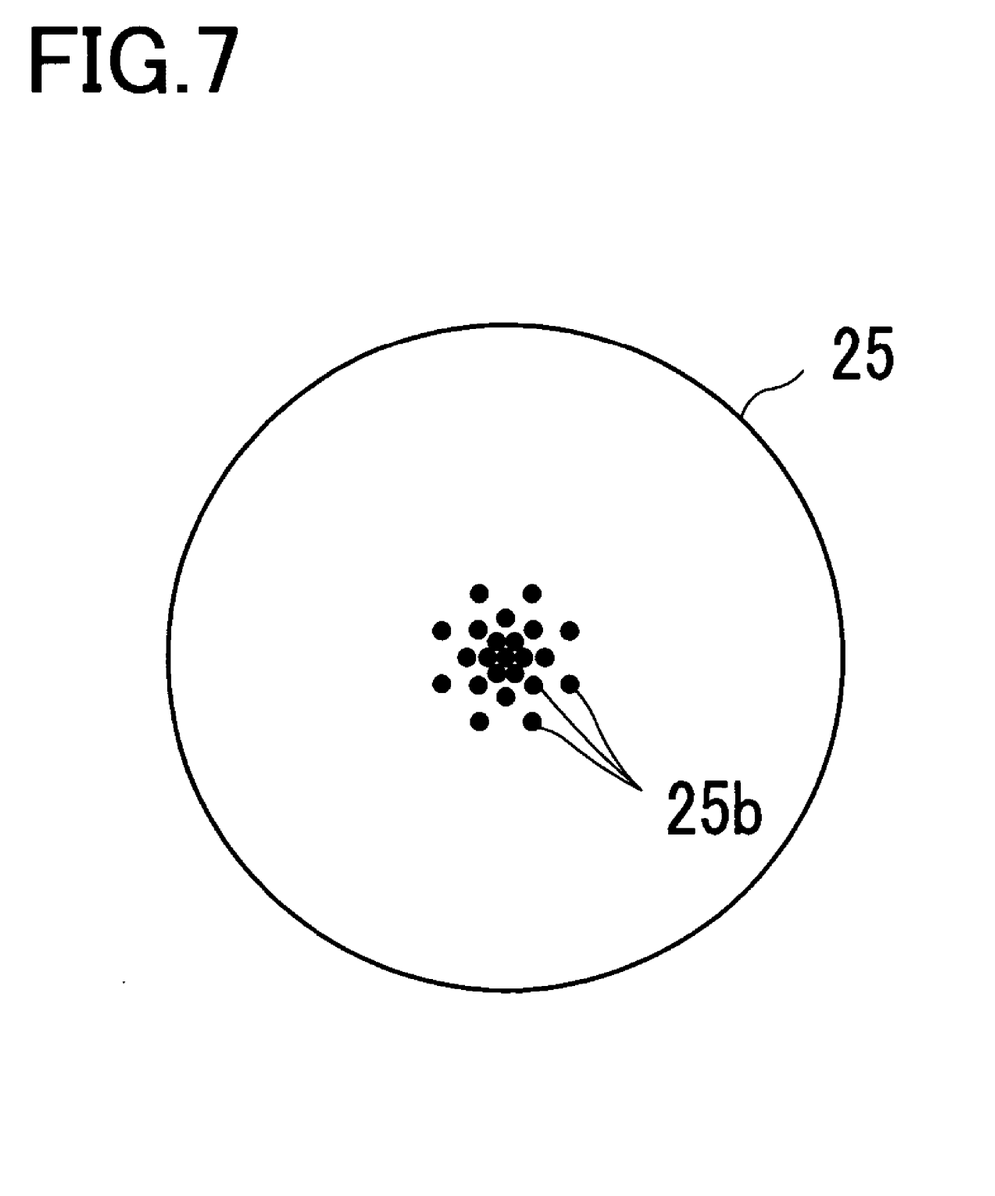
FIG. 7 is a structural view of a modification example of the beam-attenuating plate.

The beam-attenuating plate 25 is made of a glass plate with a black point of 1.5 mm in diameter coated as the shielding part 25a. The size of the black point, which is not limited to the above, may be changed according to a desired intensity in the center portion of the irradiation spot. As shown in FIG. 7, the beam-attenuating plate 25 may be provided with a shielding part 25b consisting of a plurality of black points so as to produce a desired value of the intensity in the center portion of the irradiation spot.

Besides the beam-attenuating plate 25 having the shielding part 25a which blocks 100% of the treatment beam, the beam-attenuating member may be constructed of a beam-attenuating filter having a lower transmittance in the center portion than in the peripheral portion. For example, the beam-attenuating plate 25 is designed such that the area of the shielding part 25a is half the sectional area of the on-axis luminous flux L1 at the position of the shielding part 25a. As an alternative design, the beam-attenuating filter may be designed to centrally include the beam-attenuating portion having the same size as the sectional area of the on-axis luminous flux L1 at the position of beam-attenuating portion and having a transmittance of 50% in a peripheral portion. In this case, similarly, this beam-attenuating filter can produce an intensity distribution of the irradiation spot close to that in the beam-attenuating plate 25.

As explained above, according to the present invention, the treatment laser beam can be irradiated at an appropriate irradiation intensity distribution according to treatment purposes.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. A laser treatment apparatus including:
   a laser light source, and
   a light guiding optical system, having an optical axis, for guiding a treatment laser beam emitted from the laser light source to a treatment part,
   wherein the light guiding optical system includes:
      an optical fiber through which the treatment beam emitted from the laser light source is guided;
      a variable magnification optical system which changes a magnification of an image of an exit end face of the optical fiber to be formed on the treatment part in order to change a size of an irradiation spot of the treatment beam on the treatment part;
      a condensing lens for forming an image of an exit end face of the optical fiber onto the treatment part; and
      a beam-attenuating member having a transmittance property that a transmittance is lower in a center portion than in a peripheral portion, the beam-attenuating member being placed in a position on the optical axis where the beam-attenuating member is unconjugated with the treatment part and where an on-axis luminous flux and an off-axis luminous flux of the treatment beam emerging from the exit end face of the optical fiber pass through the beam-attenuating member at different ratios.

2. The laser treatment apparatus according to claim 1, wherein the transmittance property and the position of the beam-attenuating member are determined so as to attenuate the on-axis luminous flux while not attenuating an outermost off-axis luminous flux when the irradiation spot size is set at a maximum by a variable optical system and so as to attenuate both the on-axis luminous flux and the outermost off-axis luminous flux at substantially the same ratio when the irradiation spot size is set at a minimum by the variable optical system.

3. The laser treatment apparatus according to claim 2, wherein the variable magnification optical system changes the irradiation spot size in a range of at least 50 µm to 500 µm in diameter.

4. The laser treatment apparatus according to claim 1, wherein the variable magnification optical system changes the irradiation spot size in a range of at least 50 µm to 500 µm in diameter.

5. The laser treatment apparatus according to claim 1, wherein the transmittance property and the position of the beam-attenuating member are determined so as to change a beam-attenuating ratio between the on-axis luminous flux and the off-axis luminous flux in association with a change in the irradiation spot size by the variable magnification optical system.

6. The laser treatment apparatus according to claim 1, wherein the beam-attenuating member includes a shielding part for blocking the treatment beam, the shielding part is provided centrally on the beam-attenuating member and on the optical axis.

7. The laser treatment apparatus according to claim 6, wherein the shielding part is adapted to have a size so that a part of the on-axis luminous flux is blocked.

8. The laser treatment apparatus according to claim 7, wherein the shielding part is adapted to have a size so that a beam-attenuating ratio of the on-axis luminous flux at the position of the shielding part corresponds to an intensity ratio between the center portion and the peripheral portion of the irradiation spot.

9. The laser treatment apparatus according to claim 6, wherein the shielding part is provided in the position on the optical axis where the on-axis luminous flux and the off-axis luminous flux do not coincide in a vertical plane to the optical axis.

10. The laser treatment apparatus according to claim 1 including an ophthalmic laser treatment apparatus for performing at least one of a retinal photocoagulation treatment and an iris incision treatment.

* * * * *